United States Patent
Lulla et al.

(10) Patent No.: US 8,464,914 B2
(45) Date of Patent: Jun. 18, 2013

(54) VALVE FOR AN AEROSOL DEVICE

(75) Inventors: Amar Lulla, Maharashtra (IN); Xerxes Rao, Maharashtra (IN)

(73) Assignee: CIPLA Limited, Mumbai (IN)

( * ) Notice: Subject to any disclaimer, the term of this patent is extended or adjusted under 35 U.S.C. 154(b) by 391 days.

(21) Appl. No.: 12/733,310

(22) PCT Filed: Nov. 20, 2007

(86) PCT No.: PCT/GB2007/004426
§ 371 (c)(1),
(2), (4) Date: Jul. 16, 2010

(87) PCT Pub. No.: WO2009/027618
PCT Pub. Date: Mar. 5, 2009

(65) Prior Publication Data
US 2011/0000486 A1  Jan. 6, 2011

(30) Foreign Application Priority Data
Aug. 24, 2007 (IN) .......................... 1635/MUM/2007

(51) Int. Cl.
*B65D 83/00* (2006.01)
(52) U.S. Cl.
USPC .................................. 222/402.2; 222/402.24
(58) Field of Classification Search
USPC .......... 128/200.23; 222/402.1, 402.2, 402.24; 604/140
See application file for complete search history.

(56) References Cited

U.S. PATENT DOCUMENTS

| | | | |
|---|---|---|---|
| 2,957,611 A | | 10/1960 | Sagarin |
| 4,030,644 A | * | 6/1977 | Creighton ...................... 222/396 |
| 5,881,929 A | * | 3/1999 | Coerver, Jr. ................ 222/402.1 |
| 6,131,777 A | | 10/2000 | Warby |
| 6,338,339 B1 | | 1/2002 | Tsutsui et al. |
| D631,956 S | * | 2/2011 | Lulla et al. ................... D24/110 |
| 2002/0158087 A1 | * | 10/2002 | Tsutsui et al. ............. 222/402.1 |
| 2006/0243753 A1 | * | 11/2006 | Goujon et al. ............. 222/402.2 |
| 2010/0275912 A1 | * | 11/2010 | Lulla et al. ............... 128/203.12 |

FOREIGN PATENT DOCUMENTS

| FR | 2840890 | 12/2003 |
|---|---|---|
| JP | 57209666 | 12/1982 |
| WO | WO 2004096666 A1 * | 11/2004 |

OTHER PUBLICATIONS

English Abstract of FR2840890.
English Abstract of JP57209666.

* cited by examiner

*Primary Examiner* — Kevin P Shaver
*Assistant Examiner* — Patrick M Buechner
(74) *Attorney, Agent, or Firm* — Dykema Gossett PLLC (57) ABSTRACT

A valve for an aerosol device includes a valve assembly receivable in an opening provided in a container of the aerosol device to close the opening and includes a seal between the valve assembly and the container.

9 Claims, 5 Drawing Sheets

VALVE FOR AN AEROSOL DEVICE

BACKGROUND OF THE INVENTION

1. Field of the Invention

The present invention relates to a valve for an aerosol device, and more specifically, but not exclusively, to a valve for an aerosol device for a metered dose inhaler.

2. The Prior Art

The term aerosol is considered to encompass all types of pressurized containers used for delivery of aerosolized products meant for a variety of medical and non-medical applications including, but not limited to, drugs, cosmetics (deodorants, hair sprays, hair mousses, shaving creams), perfumes, air fresheners, insect repellents, cleaning agents, paints, lubricants and the like. Aerosol devices may deliver aerosolized, ingredients in an uneven or continuous manner delivering varying quantities per actuation, or in a uniform manner, delivering predetermined identical quantities, or doses, per actuation.

A metered dose inhaler is a dispenser designed to deliver a specific dose of medication to a user with each usage.

Typically, aerosol devices comprise a container and a valve crimped on the container. The valve is fitted to the body of the container by crimping a valve ferrule against the body of the container with an intermediate seal made of an elastomeric material compressed between the body and the ferrule. The process of positioning a valve in place and crimping around it to form a seal and close the container is time consuming. Aerosol devices produced in this way are prone to leakages resulting from improper sealing of the valve and the body of the container. Aside from the difficulty in obtaining an efficient seal, the step of crimping involves a considerable amount of production time during the manufacture of such devices. Frequent testing of the devices must be conducted throughout the manufacturing process to ensure that leaks are not present. This all requires extra skilled man-power and machinery, thereby increasing the overall cost and time required for the production.

The problem of leaks is especially significant in the case of medicinal aerosol formulations. In medicinal aerosol formulations it is important to ensure that an appropriate concentration of the drug in the container is maintained throughout the entire usage period. Leakage of the propellants in such devices can lead to non-uniform and unpredictable drug delivery, which is a serious problem with these devices.

It is common in many aerosol devices to use thermoplastic elastomers as an additional means to obtain a more effective seal. However, in aerosols meant for medicinal purposes this technique has, further drawbacks. Contact of the medication with an elastomer greatly increases the chances of drug contamination through the process of leaching. If the elastomeric elements are not incorporated, in an effort to avoid this problem, the sealing of the aerosol device through crimping is compromised, leading to increased leakage problems as discussed above.

Numerous attempts have been made to make leakage resistant aerosol devices. Various known aerosol devices incorporate an intermediate seal, either in the form of a ferrule gasket placed and compressed between the top edge of the body of the container and the opposing surface of the ferrule gasket, or of an O-ring placed around the exterior of the body of the container and compressed between the body of the container and an annular flange of the valve ferrule. Other approaches include incorporating gaskets made up of material of varying durometer values, in an attempt to achieve more effective sealing. However, the problems discussed above still remain.

It would be beneficial if a valve assembly could be provided for an aerosol device which enabled the aerosol device to be more easily sealed, while also allowing more efficient production of the aerosol device.

Conventional aerosol devices have a number of further disadvantages. In many cases, due to the shape of the container used, it is not possible for the container to dispense every last drop of a substance to be delivered. This is wasteful in all applications, but is most significant where a medicament is to be delivered by the aerosol device. Canisters for use with metered dose inhalers are designed to deliver a certain number of controlled doses of medicament to a user. The devices are commonly employed in inhaler apparatus to treat asthma and similar complaints. Since in existing canisters there is often a quantity of the medicament which cannot be delivered, the container is routinely over-filled (in some cases by up to fifteen percent). This not only increases the amount of medicament, propellant and the size of container required for a given number of doses, but also complicates the calculation of the amount of medicament required. If one could be sure of complete exhaustion of a container during use, then less medicament could be used with a smaller container, the filling of which would be simplified because only the number of doses and size of each dose would need to be known in order to determine the size/volume of container required.

It is an object of the present invention to provide a valve for an aerosol device which also serves as a closure for the aerosol device. It is a related object of the present invention to provide a valve assembly for an aerosol device which allows for nearly complete exhaustion of the substance contained in the aerosol device.

SUMMARY OF THE INVENTION

According to the present invention there is provided a valve assembly for an aerosol device, the valve assembly being receivable in an opening provided in a container of the aerosol device to close said opening, wherein means are provided on the valve assembly to form a seal between the valve assembly and a container.

The valve assembly is preferably substantially cylindrical, so as to be locatable in an open end of a substantially cylindrical container. Peripheral sealing means may then be provided around the entire periphery of the valve assembly, to provide a seal between the outside of the valve assembly and the inside of the container. Peripheral sealing of this type is preferable to so called 'face sealing', where the valve member is sealed only against a planar face of a canister. A better seal can be achieved from the periphery of a valve assembly than from simple interaction of two substantially planar surfaces. Face sealing typically also requires crimping of a ferrule with a gasket and a valve, which can cause damage to the neck of the can. The valve assembly can be held in place by a cap, positioned around and crimped or otherwise attached to the outside of the container. Due to the valve assembly closing the entire opening of the container, and due to the peripheral sealing, there is no need for the means of attaching the cap member to also serve as a seal. This results in an aerosol device which is more simply and efficiently manufactured.

Peripheral sealing is most easily achieved in an assembly where the container and valve assembly are both cylindrical in shape. Sealing elements such as elastomeric rings may be employed to achieve the seal between an exterior part of the valve element and an interior part of the container.

The valve assembly preferably has a flat portion, perhaps formed by a body part of the valve assembly, which, in use, faces towards the interior of a container. The flat end portion minimises the chances of a substance forming pools (ullage) or otherwise being prevented from being expelled from the container. To maximise the chances of expelling every drop of a substance, channels or suitable apertures should be provided on or immediately adjacent the flat surface to provide access to the interior of the valve assembly.

The component parts of the valve assembly may be arranged in a valve body and contained therein by a sealing piece, which may be snap-fit together, or joined together by other suitable means. This provides a self contained valve assembly ready for insertion into a suitable container. The component parts of the valve assembly may comprise, among others, a valve stem, a spring and a valve chamber. A space is preferably provided between the valve stem and valve chamber, to contain a volume of substance comprising one 'dose' for delivery when the valve is activated.

The component parts of the valve assembly may further comprise a seat gasket positioned between the valve chamber and the sealing piece. The seat gasket preferably surrounds the valve stem and is capable of sealing an aperture provided in the valve stem. The valve stem is preferably movable, for example slidable, within the valve chamber. By restricting the movement of the seat gasket, the aperture in the valve stem can be sealed and unsealed as the valve stem moves within the valve chamber.

The valve assembly is particularly suitable for application to aerosol devices containing medicament to be delivered to a patient, for example in the form of MDI canisters.

BRIEF DESCRIPTION OF THE DRAWINGS

Aspects of the invention will be better understood with reference to the following detailed description of a preferred embodiment. The detailed description is included by way of example only, and is not intended to limit the protection sought. Throughout the detailed description reference is made to the accompanying drawings, in which.

DETAILED DESCRIPTION OF THE PREFERRED EMBODIMENTS

Figure 1:
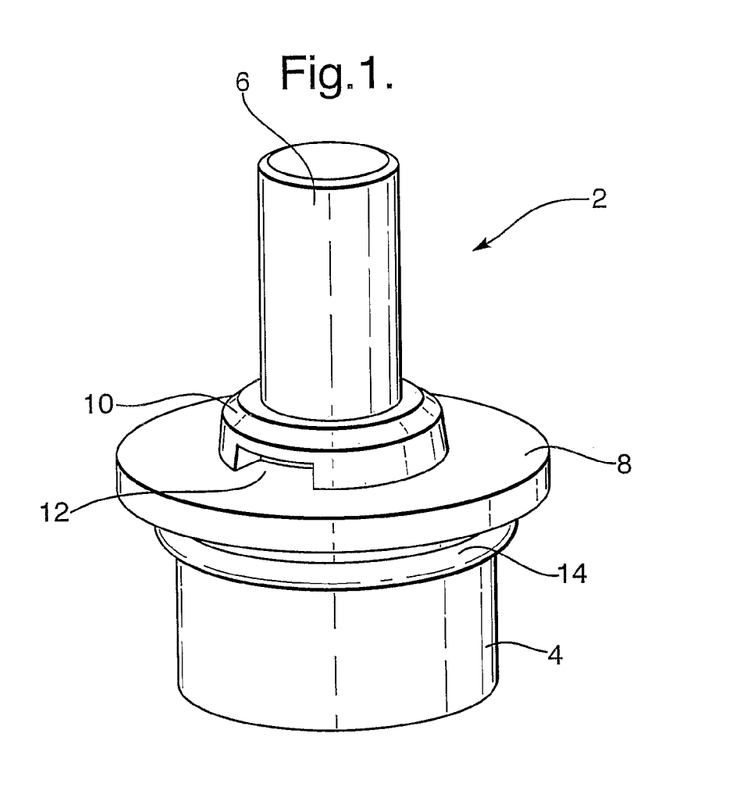
FIG. 1 is a perspective view of a valve body from a valve assembly of an aerosol device according to a first embodiment of the present invention.

The valve body 2 of FIG. 1 comprises an open hollow tubular section 4 at one end, and an enclosed tubular section 6, of a smaller diameter, at the other. On the interior of the valve body 2, the tubular sections 4,6 join up such that the valve body 2 is substantially hollow. Between the two tubular sections 4,6, to the exterior of the valve body 2, a circular disc shaped flange 8 is provided. On the side of the flange 8 adjacent the closed tubular section, a raised area 10 is provided, with two apertures 12 on opposite sides thereof.

The apertures 12 are in the form of slots which run against the flat surface of the flange 8 and provide fluid communication between the outside and the inside of the valve body 2. A circumferential ridge 14 is provided to the exterior of the open tubular section 4 of the valve body 2.

Figure 2:
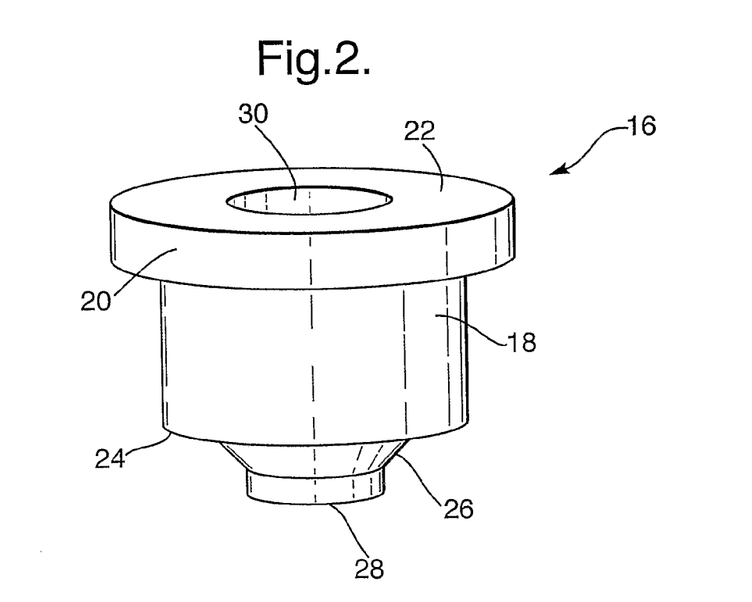
FIG. 2 is a perspective view of a valve chamber from the valve assembly of said device according to a first embodiment of the present invention.

FIG. 2 shows a valve chamber 16 which, in use, fits inside the open tubular section 4 of the valve body 2 of FIG. 1. The valve chamber 16 has a main cylindrical section 18 with an external diameter substantially equal to the internal diameter of the open tubular section 4 of the valve body 2. At one end of the cylindrical section 18 there is a circular flange 20 which is sized to rest on a lip provided on the interior of the open tubular section 4 of the valve body 2, adjacent the open end. Accordingly, the flat end section 22 of the flange 20 finishes flush with the open end of the open tubular section 4 of the valve body 2 when the valve body 2 and valve chamber 16 are assembled.

At the end of the cylindrical section 18 opposite the flange 20, a square shoulder 24 is provided. Radially inward from the square shoulder, a truncated cone section 26 narrows the outer diameter of one end of the valve chamber 16 to a circular opening 28 which leads to an axial tubular bore 30 running through the centre of the valve chamber 16, emerging at the centre of the flange 20. The opening 28 at the end of the valve chamber 16 is of a smaller diameter than the bore 30 which runs through the valve chamber 16, and out of the centre of the flange 20.

Figure 3:
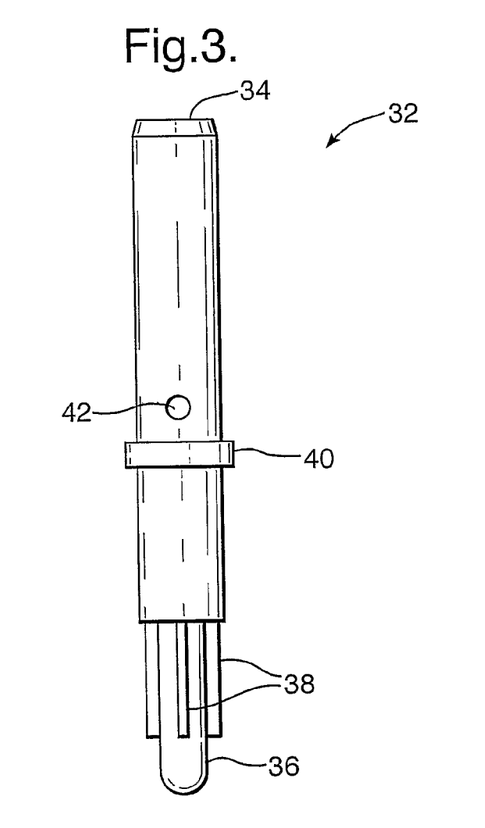
FIG. 3 is a perspective view of a valve stem from a valve assembly of said device according to a first embodiment of the present invention.

FIG. 3 shows a preferred valve stem 32 which, in use, is positioned in the bore 30 of the valve chamber 16. The valve stem 32 is essentially a thin tubular part, with one end enclosed. The open end 34 of the tube is the part of the valve assembly through which a substance is expelled during use. The closed end 36 of the tube is opposite to the open end 34, and is of a smaller diameter. Four radially extending fins 38 are provided on a part of the closed end 36 of the valve stem 32, spaced slightly from the end. The fins 38 give an effective external diameter larger than the closed end 36 of the valve stem 32, but slightly smaller than its main hollow section. A flange 40 is provided approximately half way along the valve stem 32. To the side of the flange 40 adjacent the open end 34 of the valve stem 32 there is a small aperture 42. The aperture 42 provides fluid communication with the hollow section of the valve stem 32.

The external diameter of the hollow part of the valve stem 32 is slightly smaller than that of the opening 28 at the end of the valve chamber 16 adjacent the truncated cone section 26. However, the diameter of the flange 40 is slightly larger than the opening 28 at the end of the valve chamber 16, but slightly smaller than the internal diameter of the bore 30 which runs through the valve chamber 16. The significance of this will be explained below.

Figure 4:
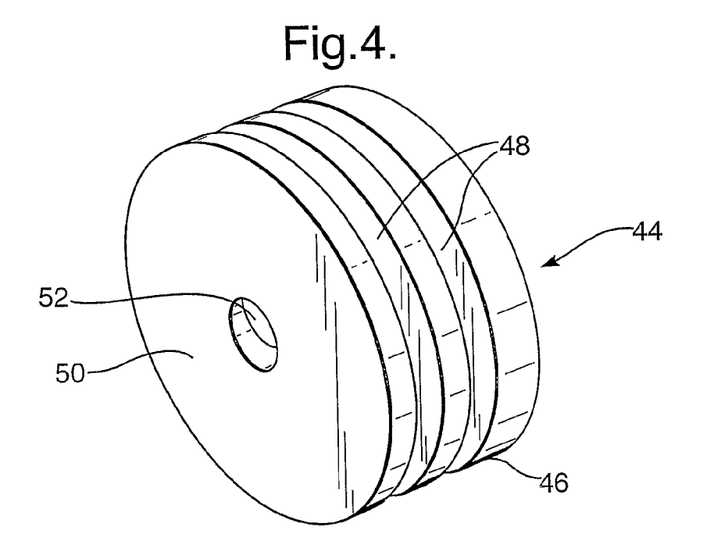
FIG. 4 is a perspective view of a sealing piece from a valve assembly of said device according to a first embodiment of the present invention.

The sealing piece 44 shown in FIG. 4 comprises a section of tube 46 which is largely closed at one end. In use, it fits over the open hollow tubular section 4 of the valve body 2. The internal diameter of the sealing piece 44 is substantially the same as the external diameter of the open hollow tubular section 4 of the valve body 2, to ensure a slight interference fit therebetween. The interior surface (not shown) of the sealing piece 44 further comprises a circumferential channel to engage with the circumferential ridge 14 of the valve body 2. Two further circumferential channels 48 are provided on the outside wall 46 of the sealing piece 44 to accommodate elastomeric sealing rings (not shown). The largely closed end of the sealing piece 44 is provided as a flat disc-like end 50 having a small circular hole 52 in the centre. The small hole 52 is just large enough for the hollow part of the valve stem 32 to pass through.

The interaction of the various parts of the valve assembly described in FIGS. 1-4 will now be described in relation to the exploded view of FIG. 5.

Figure 5:
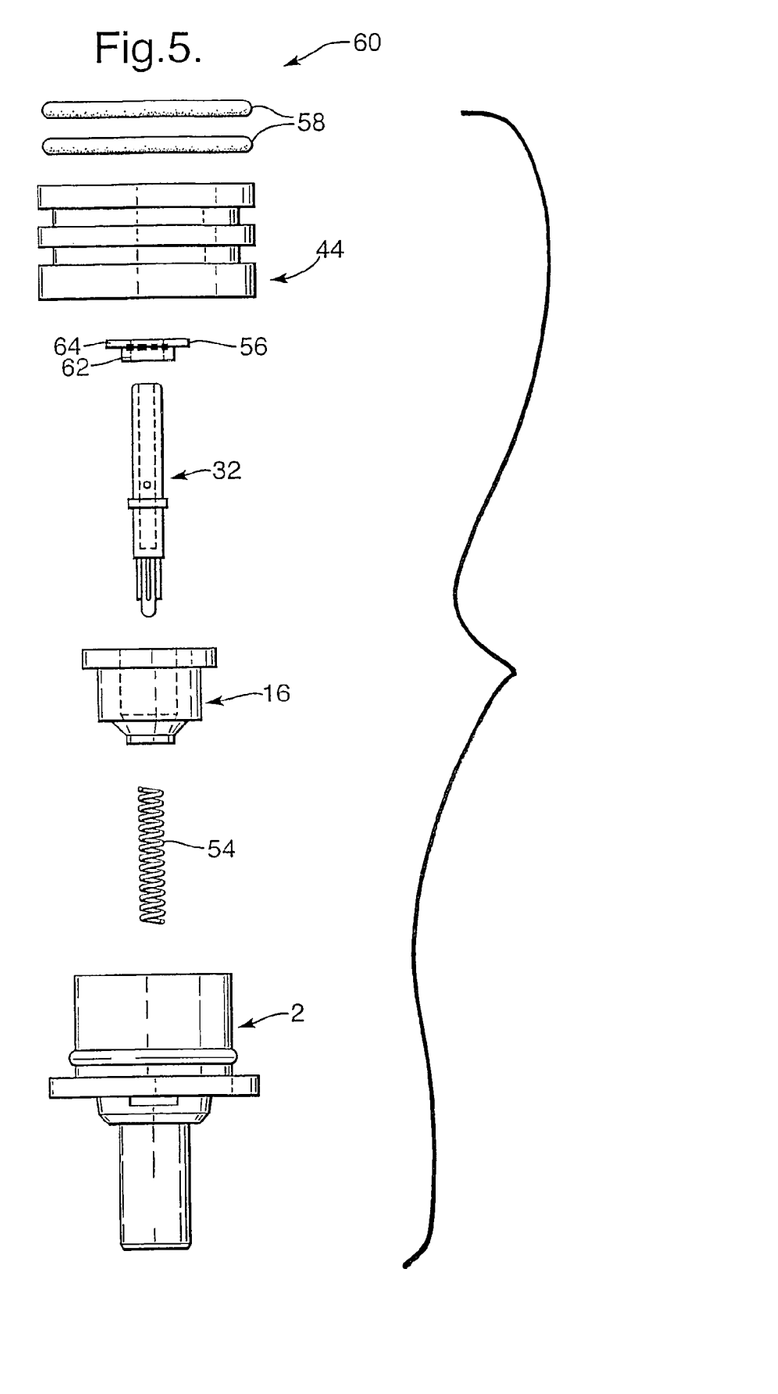
FIG. 5 is an exploded view of a valve assembly of said device according to a first embodiment of the present invention, including the parts shown in FIGS. 1-4.

FIG. 5 shows a front view of the various components that make up a valve assembly 60 in accordance with the present invention. Along with the valve body 2, valve chamber 16, valve stem 32 and sealing piece 44 described previously, the assembly further comprises a spring 54, a seat gasket 56 and two elastomeric sealing rings 58. For the sake of simplicity in the drawings, the reference numbers for various individual parts of the components shown in FIG. 5 are not shown on the exploded view. The reader is referred back to FIGS. 1-4.

The assembly of the valve assembly 60 is relatively straightforward. The spring 54 is inserted into the valve body 2 where it locates in the enclosed tubular section 6. The valve stem 32 is inserted into the valve chamber 16 so that the closed end 36 of the valve stem 32 passes through the opening 28 in the valve chamber 16. The seat gasket 56 is positioned on the valve stem 32 so that it abuts the flange 40. In this position, the seat gasket 56 covers the aperture 42 in the side of the valve stem 32. The seat gasket has a stepped cross section, the smaller diameter part 62 of which sits against the flange 40 on the valve stem 32, and is sized so as to fit inside the bore 30 of the valve chamber. The larger diameter part 64 rests on top of the flange 20 of the valve chamber 16.

The valve chamber 16, with the valve stem 32 and seat gasket 56 in place, is then lowered into the valve body 2. The closed end 36 of the valve stem 32 engages with the spring 54, which is supported against the radially extending fins 38 of the valve stem 32. Once the valve chamber 16 has been pushed firmly into position inside the valve body 2, the sealing piece 44, with elastomeric sealing rings 58 in position in its external circumferential channels 48, is pushed into place around the outside of the valve body 2 such that the circumferential ridge 14 of the valve body 2 engages with the internal circumferential channel (not shown) of the sealing piece 44. The valve assembly 60 then forms a complete self contained unit.

Because the hollow section of the valve stem 32 is of a slightly greater diameter than the effective diameter of the radially extending fins 38, the valve stem 32 tends to naturally sit in the valve chamber 16 such that only the closed end 36 of the valve stem 32 and the radially extending fins 38 extend beyond the opening 28 in the valve chamber 16. The hollow portion of the valve stem 32 is capable of passing through the opening 28, but due to its greater diameter some further impetus (force) is require to make it do so. The result of this is that, when the valve assembly 60 is in its complete state, a force applied to the open end 34 of the valve stem must overcome not only the resistive force of the spring 54, but also the additional resistance caused due to the change in diameter of the valve stem 32. This provides a greater initial resistance than the spring 54 alone, which is helpful in avoiding accidental actuation of the valve assembly 60. When the external force is removed, the restoring force of the spring 54 is sufficient to return the valve stem 32 to its rest position. The flange portion 40 of the valve stem 32 is too large to pass through the opening 28 in the valve chamber 16, and so provides a stop to avoid over actuation of the valve stem 32.

Figure 6:
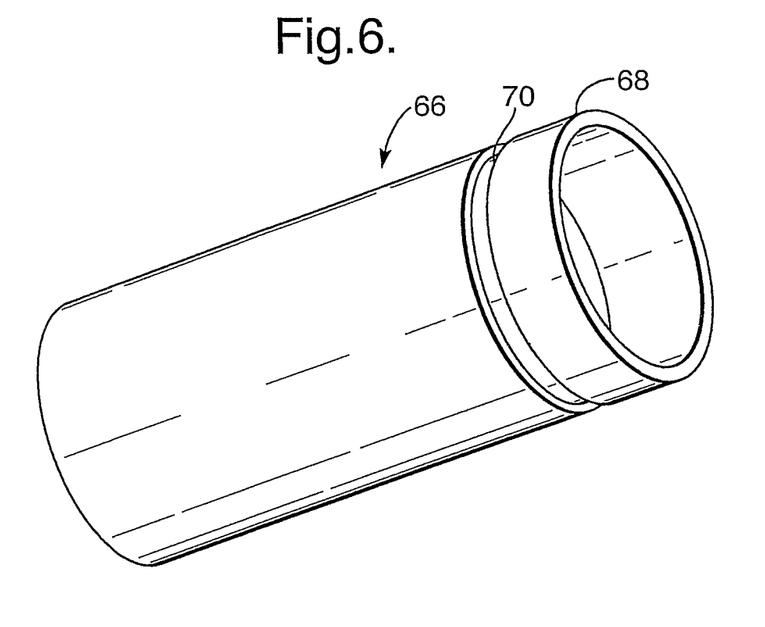
FIG. 6 is a perspective view of a container of said device according to a first embodiment of the present invention.

The container 66 shown in FIG. 6 is configured to receive the valve assembly 60 described above. The container 66 has a simple cylindrical shape and is enclosed at one end only. The open end 68 of the container 66 is sized to receive the valve assembly 60. The internal diameter of the open end 68 is substantially the same as, or slightly smaller than, the external diameter of the complete valve assembly 60, including the elastomeric sealing rings 58. A lip (not shown) is provided on the interior of the container 66 to support the valve assembly 60. The lip is positioned such that the flat disc like end 50 of the sealing piece 44 of the valve assembly 60 is positioned flush with the opening of the container 66 once assembled. A circumferential groove 70 is provided in the outside wall of the container 66 adjacent the open end 68.

Figure 7:
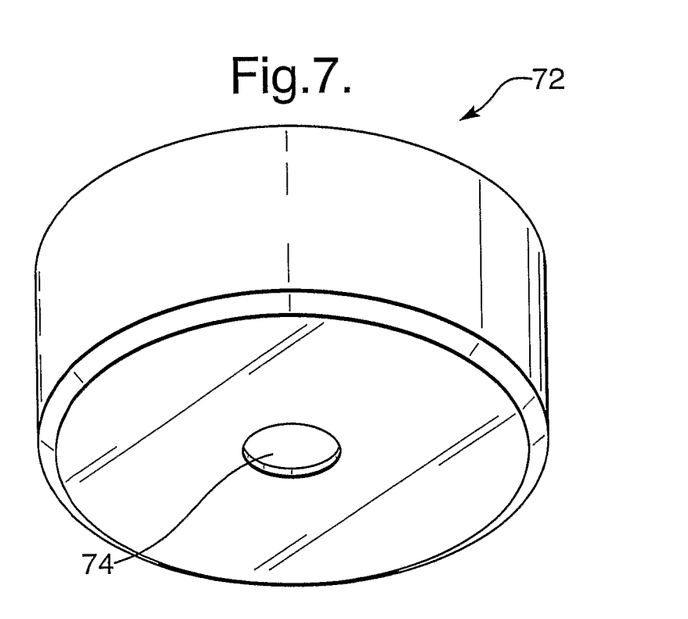
FIG. 7 is a perspective view of an end cap of said device according to a first embodiment of the present invention.

The metal end cap 72 shown in FIG. 7 is designed to be placed over the open end 68 of the container 66 once the valve assembly 60 is in place, in order to form a complete aerosol device. The end cap 72 takes the form of a cylinder with one flat substantially closed end face with a hole 74 provided in the centre. The end cap 72 can be crimped or attached by some other means to the container 66. Where crimping is used, the forces involved can be much less than in typical aerosol manufacture. This is because the end cap 72 of the present invention need not serve any sealing purpose, but merely has to retain the valve assembly 60 in position in the container 66. Furthermore, there is no need to apply any crimping force directly to the valve assembly 60, so the possibility of causing damage to the valve is minimised.

Figure 8:
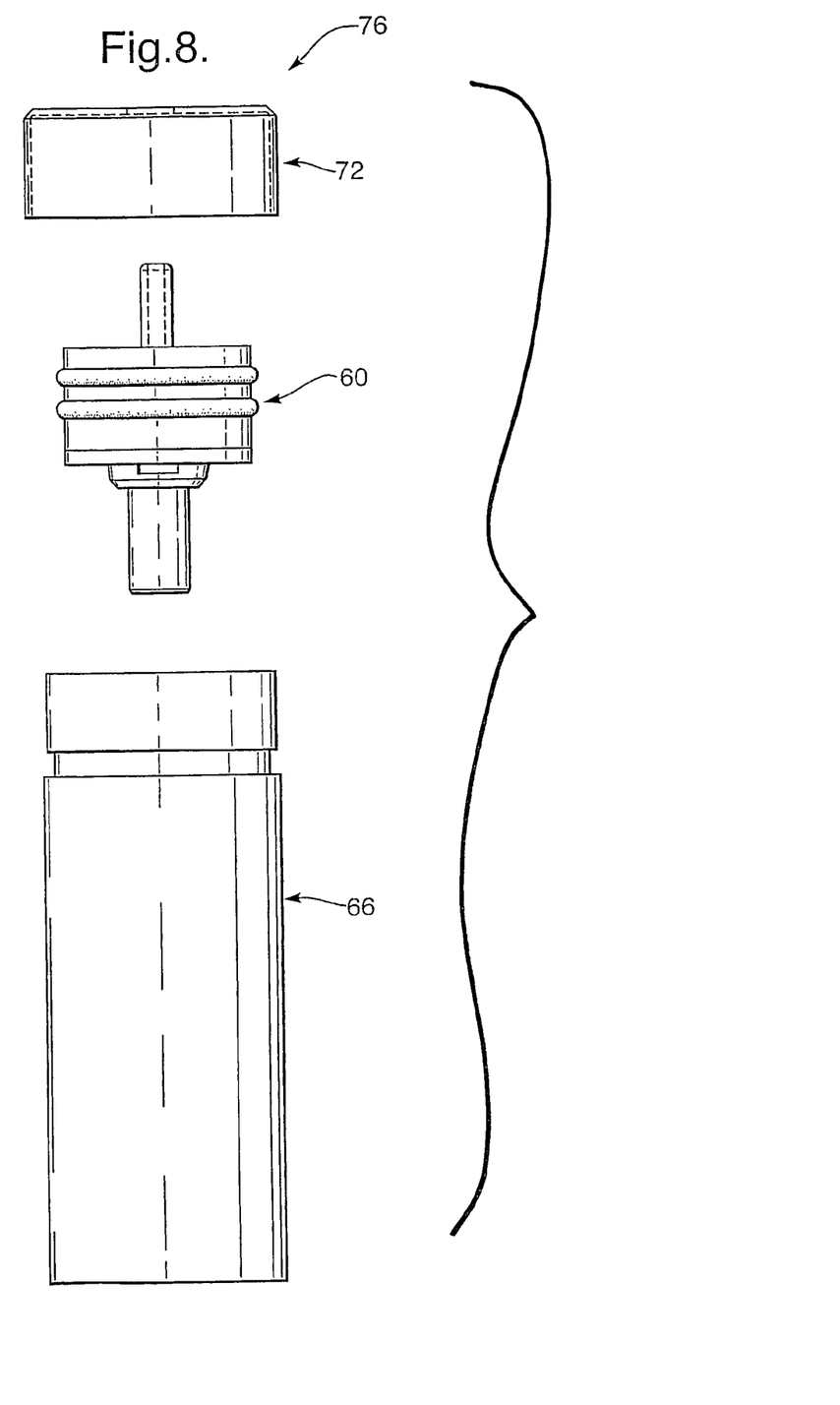
FIG. 8 is an exploded view of said aerosol device according to a first embodiment of the present invention.

The final assembly of the aerosol device 76 will be understood with reference to FIG. 8. FIG. 8 shows front views of the container 66, the end cap 72 and the complete valve assembly 60.

The valve assembly 60 is inserted into the open end 68 of the container 66, such that it rests on the internal lip (not shown) provided therein. The elastomeric sealing rings 58 of the valve assembly 60 form a seal around the entire circumference of the valve assembly 60. The end cap 72 is then placed over the end of the container 66 with the valve stem 32 extending out through the hole 74, and crimped into the circumferential groove 70 provided on the container 66 to retain the valve assembly 60 in place. If better joining is required then further elastomeric elements may be incorporated between the end cap 72 and the container 66. Alternatively, or additionally, one or more further circumferential grooves may be provided in the exterior surface of the container.

Once the aerosol device 76 is complete, it can be filled through the valve ready for use. It should be noted that, although the assembly of parts of the aerosol device 76 is shown in the drawings with the valve positioned at the top, in use it is likely that the aerosol device will be inverted from this position. In this regard, it is significant that one side of the flange, disc 8 will provide a flat base for the inside of the aerosol device. Referring back to FIG. 1, the flat flange disc has, on one side, a raised portion 10 with two slot shaped apertures 12 therein. The slots 12 run flat along the face of the flange 8 into the interior of the valve body 2. Given that the face of the flange 8 will form a flat base of the aerosol device 76 when in use, the positioning of the slots 12 allows for all of the contents of the aerosol device 76 to be exhausted. There is nowhere in the device for a substance to 'pool' and not be in communication with an aperture.

Once the substance passes through the slots 12 in the valve body 2, it then moves into contact with the valve chamber 16. Because of the seating of the valve stem 32 in the opening 28 of the valve chamber 16, the substance is able to pass through the gaps between the radially extending fins 38 of the valve stem 32 and through the opening 28 in the valve chamber 16. A small amount of the substance is, therefore, present in the clearance volume between the exterior of the valve stem 32 and the interior of the valve chamber 16. This constitutes a single 'dose' to be exhausted from the aerosol device 76. The substance is prevented from leaving the clearance volume by the seat gasket 56, which seals not only the end of the bore 30 of the valve chamber 16, but also the small aperture 42 in the side of the valve stem 32.

When the valve stem 32 is subjected to an external force, it is pushed into the remainder of the valve assembly 60 against the force of spring 54. As the hollow part of the valve stem 32 passes through the opening 28 in the valve chamber 16, the valve chamber 16 is sealed off from the valve body 2 and, therefore, from the container 66. The movement of the valve stem 32 also causes the aperture 42 in the side of the valve stem to be uncovered, since the seat gasket 56 remains in place due to the interaction of its larger diameter part 64 with the flat surface 22 of the flange 20 of the valve chamber 16, as the valve stem 32 is depressed. This allows the substance contained in the clearance volume between the valve stem 32 and the valve chamber 16 to enter the hollow part of the valve stem through aperture 42, and be expelled through the open end 34 of the valve stem 32 in the form of a fine mist or spray.

The invention consists of a number of distinct features which are, for the sake of brevity, described in the context of one preferred embodiment. It should be appreciated that the various features are advantageous in their own right and may be provided separately or in a suitable alternative combination.

The material for making the valve may be at least one selected from a group of materials consisting of metals; glass; thermoplastics materials including but not limiting to polymers such as PET, polycarbonates, polysulphones and the like and any combinations thereof. Alternatively, the valve assembly may be made of acetyl or polyester, Hytrel®, or the like.

The elastomeric materials used in the valve assembly may be at least one of nitrile, butyl, chloroprene, EPDM, TPE, HNBR, POE, chlorobutyl, and bromobutyl or any other thermoplastic elastomer.

The various component parts of the valve assembly may be made by any appropriate manufacturing techniques. In the case of parts made of a plastics material, molding techniques including, but not limited to, injection molding, two stage blow molding, compression molding, transfer molding, extrusion molding, blow molding, rotational molding or thermoforming are preferred.

If the container used with the valve assembly is formed of an at least partially transparent plastics material, e.g. a polysulphone, a user can readily see how much substance is in the container at any given time.

The invention claimed is:

1. A valve assembly for an aerosol device, the valve assembly, in use, being receivable in an opening provided in a container of the aerosol device to close said opening, the valve assembly comprising:
   means on an outside of the valve assembly or providing a seal with the container when positioned in the opening thereof;
   a flat portion which, in use, faces towards the interior of the container and provides a flat base for an interior of the aerosol device;
   channels immediately adjacent the flat portion which provide access to an interior of the valve assembly;
   wherein component parts of the valve assembly comprise a valve stem, a spring and a valve chamber, and are arranged in a valve body contained therein by a sealing piece to provide a self-contained valve assembly; and
   wherein the valve stem and the valve chamber define a space therebetween that contains one dose to be released when the valve assembly is actuated.

2. The valve assembly according to claim 1, wherein a part of the valve assembly is cylindrical.

3. The valve assembly according to claim 1, wherein said means for providing a seal extends completely around a periphery of the valve assembly.

4. The valve assembly according to claim 1, wherein the flat portion is formed by a body part of the valve assembly.

5. The valve assembly according to claim 1, wherein the valve body and the sealing part are snap-fit together.

6. The valve assembly according to claim 1, wherein the component parts of the valve assembly comprise a seat gasket positioned between the valve chamber and the sealing piece.

7. The valve assembly according to claim 6, wherein the seat gasket surrounds the valve stem and is capable of sealing an aperture provided in the valve stem.

8. The valve assembly according to claim 1, wherein the valve stem is movable within the valve chamber.

9. The valve assembly according to claim 1, wherein the seal means comprises an elastomeric ring.

\* \* \* \* \*

UNITED STATES PATENT AND TRADEMARK OFFICE
CERTIFICATE OF CORRECTION

PATENT NO.       : 8,464,914 B2  
APPLICATION NO.  : 12/733310  
DATED            : June 18, 2013  
INVENTOR(S)      : Lulla et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this

Eighth Day of September, 2015

Michelle K. Lee  
*Director of the United States Patent and Trademark Office*